US006958058B1

(12) United States Patent
Hunter, Sr. et al.

(10) Patent No.: US 6,958,058 B1
(45) Date of Patent: Oct. 25, 2005

(54) METHODS AND DEVICES FOR PUMPING FLUID AND PERFORMING SURGICAL PROCEDURES

(75) Inventors: Donald W. Hunter, Sr., Somerset, PA (US); Joseph J. Cerola, Delray Beach, FL (US); Allan Coplin, Fort Lauderdale, FL (US); Reginald Fowler, Meridian, TX (US)

(73) Assignee: Medsafe Inc., Fort Lauderdale, FL (US)

( * ) Notice: Subject to any disclaimer, the term of this patent is extended or adjusted under 35 U.S.C. 154(b) by 0 days.

(21) Appl. No.: 10/454,920

(22) Filed: Jun. 5, 2003

Related U.S. Application Data

(63) Continuation-in-part of application No. 09/860,849, filed on May 18, 2001, now abandoned.

(51) Int. Cl.[7] ............................................. A61M 31/00
(52) U.S. Cl. ........................ 604/500; 604/28; 604/30; 604/35; 604/151; 417/377; 417/405; 415/141; 415/904; 418/259; 418/266
(58) Field of Search .......................... 604/131, 27, 28, 604/30, 35, 43, 500, 31, 514, 149, 151, 264, 604/246, 247, 540, 543, 249, 167.01, 167.03; 417/377, 405; 128/DIG. 12, DIG. 13; 415/141, 415/904; 418/236, 249, 141, 266, 259, 13, 418/267, 268; 433/132

(56) References Cited

U.S. PATENT DOCUMENTS

| 722,185 | A | * | 3/1903 | Robinson .................... 418/266 |
|---|---|---|---|---|
| 1,142,544 | A | * | 6/1915 | Vernon et al. ................. 418/87 |
| 4,236,589 | A | | 12/1980 | Griffith |
| 4,604,089 | A | | 8/1986 | Santangelo et al. |
| 5,125,910 | A | | 6/1992 | Freitas |
| 5,188,591 | A | | 2/1993 | Dorsey, III |
| 5,391,145 | A | | 2/1995 | Dorsey, III |
| 5,464,391 | A | | 11/1995 | DeVale |
| 5,477,494 | A | | 12/1995 | Miyagawa et al. |
| 5,484,402 | A | | 1/1996 | Saravia et al. |
| 5,542,918 | A | | 8/1996 | Atkinson |
| 5,562,640 | A | | 10/1996 | McCabe et al. |
| 5,573,504 | A | | 11/1996 | Dorsey, III |
| 5,697,773 | A | * | 12/1997 | Mendoza et al. ........... 418/236 |
| 5,718,668 | A | | 2/1998 | Arnett et al. |
| 5,807,313 | A | | 9/1998 | Delk et al. |
| 5,984,654 | A | * | 11/1999 | Mendoza et al. ........... 418/236 |
| 6,162,194 | A | | 12/2000 | Shipp |
| 6,176,847 | B1 | | 1/2001 | Humphreys, Jr. et al. |
| 6,296,459 | B1 | * | 10/2001 | Saputo et al. .......... 417/423.14 |
| 6,358,224 | B1 | | 3/2002 | Tims et al. |
| 6,419,654 | B1 | | 7/2002 | Kadan |
| 6,436,072 | B1 | | 8/2002 | Kullas et al. |

* cited by examiner

Primary Examiner—Cris L. Rodriguez
(74) Attorney, Agent, or Firm—Laurence A. Greenberg; Werner H. Stemer; Ralph E. Locher

(57) ABSTRACT

Devices and methods of use of such devices for pumping fluid and for use in surgical procedures preferably include vacuum-driven pumps for providing irrigation and suction functions to the surgical field. Such pumps may be free-standing, external to or integrated into handpieces of the surgical instruments.

22 Claims, 17 Drawing Sheets

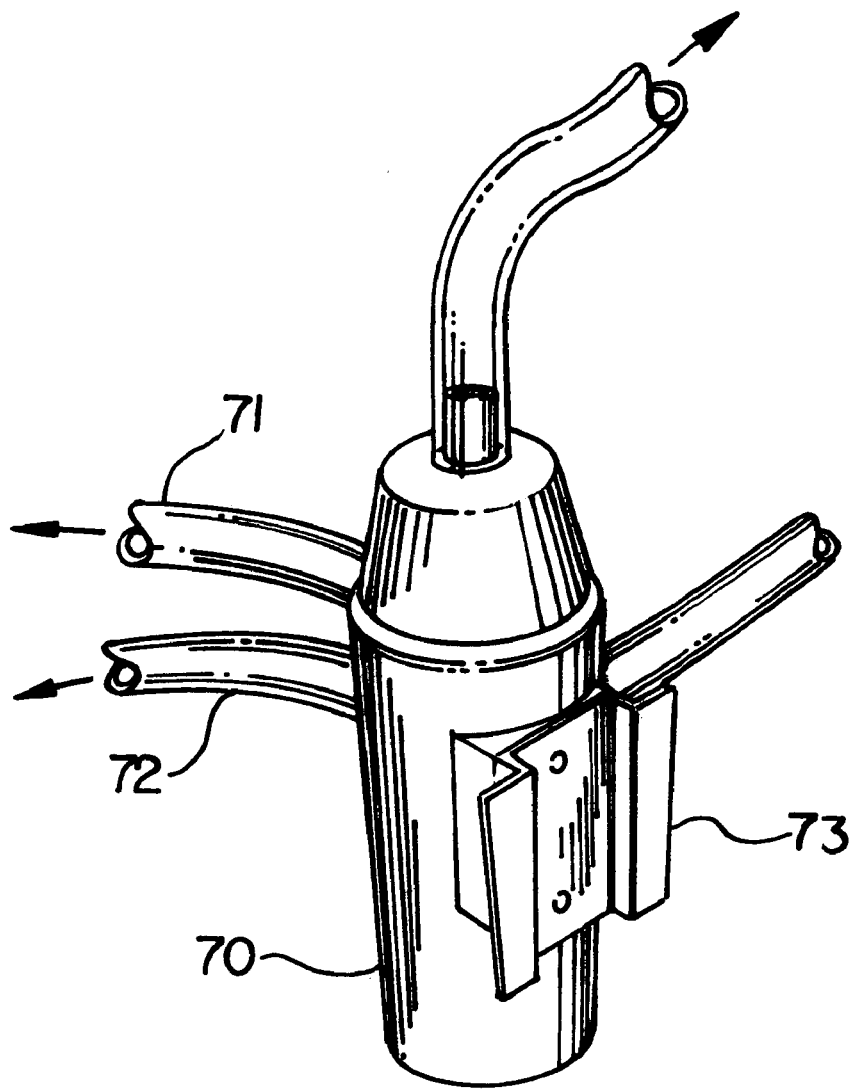
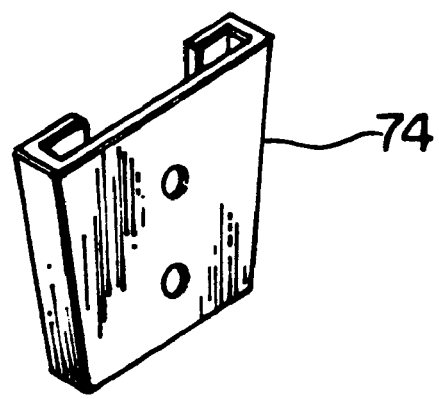
FIG. 7

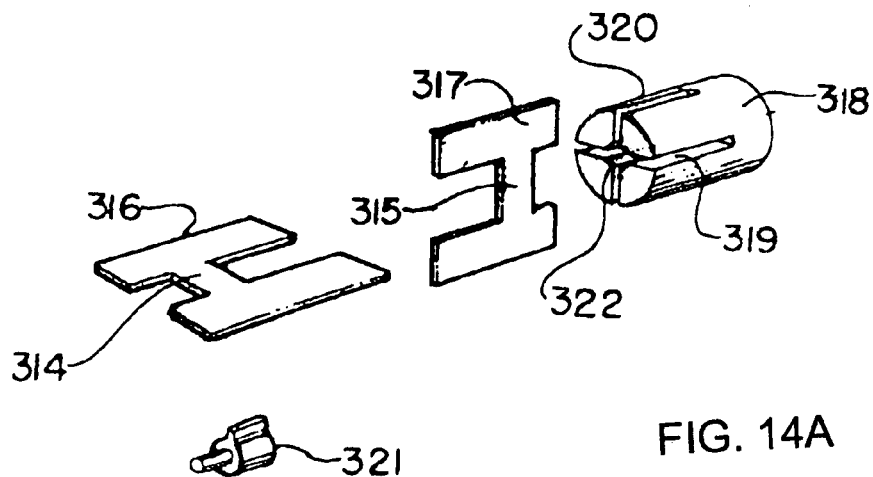
FIG. 14A
FIG. 14D
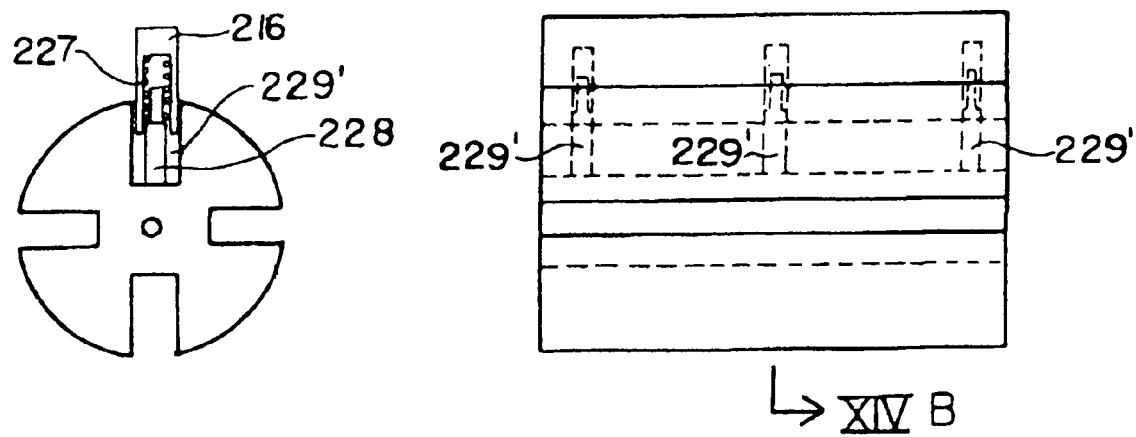
FIG. 14B
FIG. 14C

METHODS AND DEVICES FOR PUMPING FLUID AND PERFORMING SURGICAL PROCEDURES

CROSS-REFERENCE TO RELATED APPLICATION

This application is a Continuation-In-Part of application Ser. No. 09/860,849, filed May 18, 2001 now abandoned.

BACKGROUND OF THE INVENTION

Field of the Invention

The present invention relates to devices, and methods of use thereof, for surgical procedures. More particularly, the present invention relates to methods and devices for endoscopic surgical procedures requiring irrigation and suction.

Devices and methods of providing irrigation fluid and suction to a surgical site to irrigate and evacuate the tissue in the area of the surgical procedure are well known in the art. Such devices generally provide a handle member having a switching device for turning on and off the flow of the fluid provided and also for turning on and off the suction provided. Typically, both the suction source and the fluid source are individually connected through an elongated flexible tubular member to a pump or suction source which are positioned adjacent to the surgical site. Typically, the devices communicate with an external pump source to provide the fluid under pressure to the surgical site.

Minimally invasive surgery (MIS) is the art of performing surgical procedures through several small holes in the body, as opposed to open surgery, which involves an incision to expose the entire surgical field. During an MIS procedure, a sterile irrigation solution is used to wash the area to keep the operative field clean and visible. The irrigant is typically provided in sterile plastic disposable bottles or plastic intravenous bags. The suction force is provided by a vacuum that is available through a connection in the operating room wall or is provided by other measures such as a portable suction machine used in small ambulatory surgical sites.

The device used to control the irrigation and suction is called a suction/irrigation tubing set. Generally, this set consists of two lengths of tubing, one to transport the irrigant and the other for suction. The tubes are attached to a small plastic valve that usually controls the irrigation and suction with two buttons that are similar to the valves on a trumpet. Such a valving mechanism is referred to as a trumpet valve. Such trumpet valves are part of tubing kits available from Allegiance Healthcare, Part Number ASC1200, and from Davol, Inc., Part Number 5202730. Another orifice of the device is connected to a probe which is inserted into the body and performs various activities during the surgical procedures.

Irrigating solutions are pumped into the surgical field by a variety of measures. Those measures include pressurized sterile solution bottles, intravenous bags attached to squeezing mechanisms that force the fluid from the bag, and small disposable battery powered pumps that are packaged with each suction/irrigation tubing set. In addition, there are "hybrid" units which are formed of a power unit, that is connected to wall electricity in the operating room and which provides the power for the pumping unit, that is attached to the trumpet valve tubing set and is disposable.

Early irrigating devices included using solution bags that were hung above the surgical area to provide a head pressure that could be used to gently wash the surgical field. Generally, the irrigating fluid needs to be provided with more force than that supplied by simple head pressure on a fluid, and thus, irrigating fluids are provided using pumps. U.S. Pat. No. 5,484,402 to Saravia et al. teaches a self-contained pumping unit that is located adjacent to a source of irrigation and is remote from the valving handpiece device. The pumping unit includes a housing containing an outlet for liquid, a pumping member for pumping irrigation liquid through the outlet, a motor for driving the pumping member and an electric battery assembly for energizing the motor. An elongated tube connects the pumping outlet to the handpiece irrigation liquid inlet for supplying pumped irrigation liquid to the handpiece.

Another battery powered device is disclosed in U.S. Pat. No. 5,807,313 to Delk et al. A battery powered laproscopic and endoscopic irrigator is taught therein. The pumping unit includes an upper portion that connects directly to an irrigation reservoir holding an irrigation solution such as saline. A lower portion of the pump connects to the batteries. The upper portion of the pump includes a pump, a motor and attachments connecting the upper and lower portions. During the manufacturing of the pump, batteries are inserted into the lower portion and the upper portion is connected to the lower portion via clips. The pump is constructed to hang vertically from the irrigation source and to direct the irrigation fluid source downwardly with some force. There is a wire extending through the bottom of the pumping unit connecting the upper portion with the batteries and motor.

A pulsating battery pump is taught in U.S. Pat. No. 5,718,668 to Arnett et al. The handpiece contains a mechanism used to supply irrigant in a pulsating manner to the surgical site. The pump provides a reciprocally driven device for pumping pulses of irrigation liquid through an outlet device, and a powered drive device for reciprocally driving the pump.

Those battery powered pumps require the presence of switch and a wire that runs from the pump to the trumpet valve. Some battery powered pumps require a pressure switch or a manually operated switch and a wire connection between the switch and the pump. Those additional features, such as the switch and wire connection, add to the complexity of the battery powered pump and provide for sites for mechanical failure and difficulty in manufacture. Additionally, operating such a pump may add extra considerations for the surgeon during an operation.

The prior art also provides a vacuum-driven pumping device. In U.S. Pat. No. 5,542,918 to Atkinson, a fluid pump using a trumpet valve and a vacuum-driven pump is described. The pump is operated using a piston arrangement that includes springs. However, one of the disadvantages of this device is the number of parts used makes the device costly. Additionally, the device uses a pistol grip configuration rather than the more acceptable trumpet valve configuration. Also, the device must have pressure controls or it generates too much pressure for the procedures and could be dangerous.

U.S. Pat. No. 4,236,589 to Griffith discloses a vacuum motor, but has no pump which is the subject of the invention of the instant application.

U.S. Pat. No. 4,604,089 to Santangelo et al. discloses a medical irrigation system having a pump. It is stated therein that the pump may be a vacuum pump, but no details of such a pump are given.

Accordingly, what is needed are devices for surgical procedures, such as endoscopic and laparoscopic procedures, that are simple, yet provide both suction and irrigation with pressure provided by a pump that does not need an additional power source. What is also needed are methods of use of such devices to improve surgical procedures.

SUMMARY OF THE INVENTION

It is accordingly an object of the invention to provide methods and devices for pumping fluid and for performing surgical procedures, such as endoscopic and laparoscopic procedures, which overcome the hereinafore-mentioned disadvantages of the heretofore-known methods and devices of this general type and in which the devices are irrigation and suction devices that are disposable and easy to use. One embodiment of the present invention relates to a vacuum-driven pump for providing irrigating fluid under pressure to the surgical field. Another embodiment relates to a selectively controllable suction and irrigation delivery device, that is a combination trumpet valve and pump, using an alternative power source to pump pressurized fluids during surgical procedures.

Methods of use of the devices of the present invention include attaching various probes to the devices of the present invention. Those probes may include dual action functions, capable of providing suction and irrigation simultaneously, probes, with electrocautery functions, laser dissection and viewing capabilities. The present invention can be used in surgical procedures wherein suction and or irrigation is useful.

None of the prior art devices teach or suggest suction/irrigation devices that include an integrated pumping mechanism for providing the irrigating fluid under pressure as provided by the present invention. None of the prior art teaches a pump capable of being powered by using a rotating hub and blades powered by using a vacuum as in the present invention. The state of the art teaches valves and separate pumps, powered by either electricity or air pressure, but does not provide an easily manufactured, disposable valve/pump device that can provide suction and irrigating fluid under pressure higher than that provided by a head pressure, in a reliable manner. The few handpieces that do have integrated pumping mechanisms contain electric motors or have complex piston driven systems.

It is accordingly an object of the present invention to provide devices and methods for an irrigation pump having a structure that is easily manufactured.

Another object of the invention is to provide disposable devices for surgical procedures such a laparoscopy or endoscopy.

Yet another and perhaps the most important object of the present invention is to provide a stand-alone vacuum driven pump that is reliable and may be used alone or in conjunction with a trumpet valve for surgical procedures.

Still another object of the present invention is to provide devices and methods for surgical procedures that can be used in either hand of the clinician and can have interchangeable probe tips.

Yet another object of the present invention is to provide surgical procedure devices and methods that provide their own pumping action.

Another very important object of the invention is to provide devices and methods for surgical procedures that do not need additional outside power sources, other than those used by the delivery system, to pump the irrigating fluid.

An additional object of the invention is to provide for biasing the blades against an inner wall surface of a pumping chamber of the pump.

A concomitant object of the invention is to provide for conducting air at different pressures to impinge upon surfaces of the blades for rotating the blades.

Other features which are considered as characteristic for the invention are set forth in the appended claims.

Although the invention is illustrated and described herein as embodied in methods and devices for pumping fluid and for performing surgical procedures, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 7 is an external, perspective view of an embodiment of the present invention which is capable of being attached to a wall or other structure support device;

FIGS. 14A, 14B, 14C and 14D are respective exploded-perspective, cross-sectional, side-elevational and perspective views illustrating an assembly of valve blades;

DESCRIPTION OF THE PREFERRED EMBODIMENTS

Figure 1:
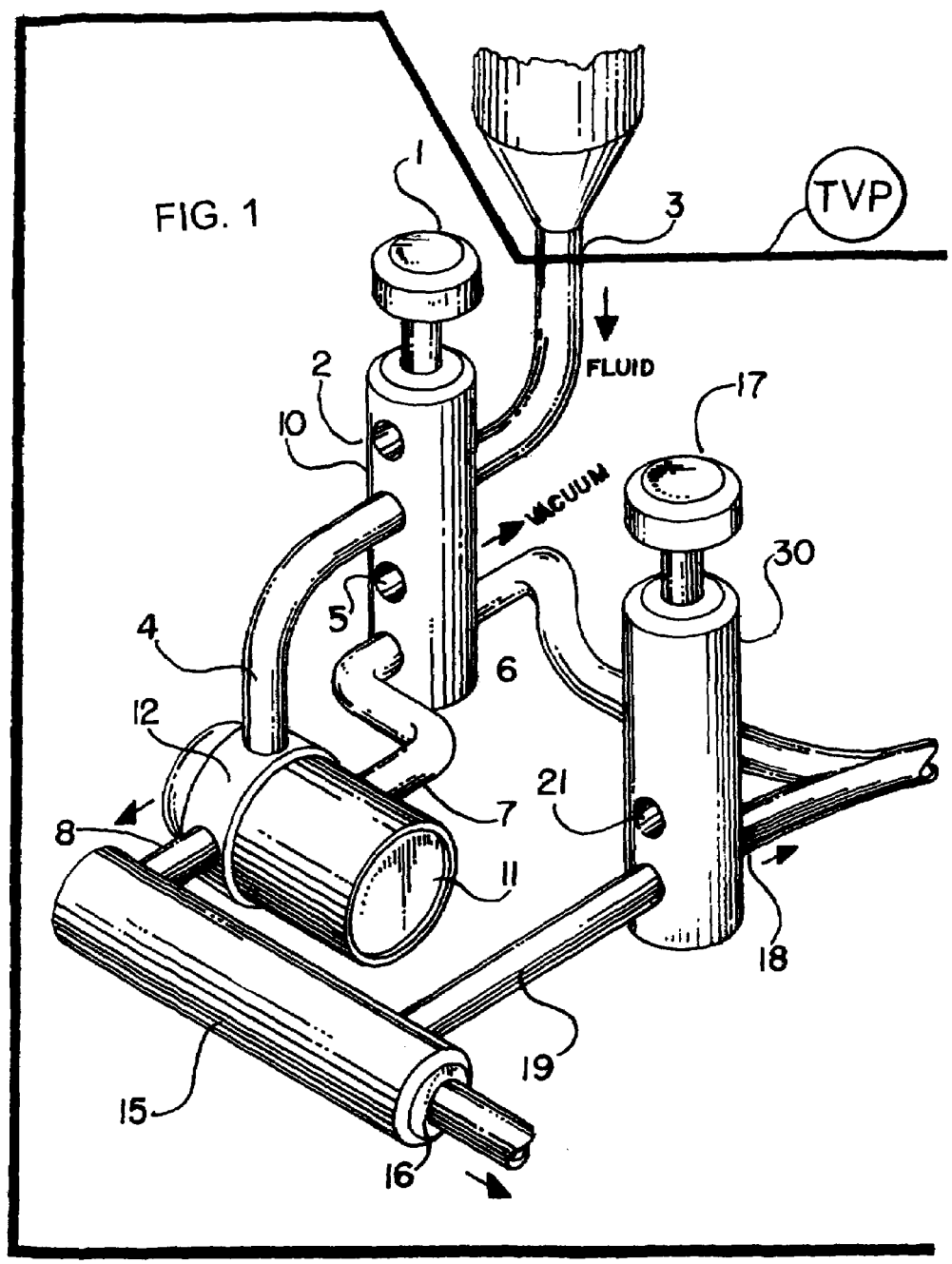
FIG. 1 is a fragmentary, diagrammatic, perspective view of the trumpet valve and pump combination of the present invention in which valves are closed.

The present invention includes devices and methods of use of such devices in surgical procedures. Surgical devices that provide irrigating fluid and suction to a surgical field are known in the art. Those devices are important to a clinician in irrigating a surgical site and evacuating debris from the site. Devices currently used in the art typically provide a handle member having a device for turning on or off the flow of the irrigating fluid, together with a device for controlling the suction. Some devices provide for simultaneous suction and irrigation. Generally, the suction source and the fluid source are connected to the device by a flexible tubing configuration and they are positioned adjacent the surgical site. Those devices provide the irrigating fluid under pressure by use of an external pumping device or provide fluid with only minimal head pressure.

The present invention includes devices that are capable of providing irrigating fluid under pressure. The present invention provides a trumpet valve and pump combination having a stand-alone pump that is vacuum-driven using a hub and movable blade system to provide irrigation for surgical procedures. Alternative embodiments of the present invention include vacuum-driven pumps that are integrated with the irrigating and suction functions of the devices.

Preferred embodiments of the present invention include vacuum-driven pumps that are separate, or external, from the irrigation fluid delivery portion of the device, such as the valve or probe portions. The irrigation/suction devices in the art, prior to the present invention, use additional sources of energy to provide the irrigating fluid under pressure or use sources that are unreliable. The energy used is either air pressure, batteries, or electricity provided in the operating theatre. External pumps may be located in areas separate from the valve device, and are disposed adjacent the surgical field by attachment to an intravenous solution bag, hanging on a support pole, or an adjacent table or stand, freestanding on the floor or attached to a wall or in the cover of a suction canister used in the operating room.

The present invention includes devices having a pumping device that is driven by a vacuum force available in the operating theatre. Such suction force may be provided by the operating theatre, either by an in-house vacuum system provided through an outlet in the room, or by suction created by any measures.

Preferably, the present invention includes a stand-alone vacuum-driven pump, external to a valve device or irrigation and suction control device. Such a preferred embodiment includes methods of placement of the pump that have attachments to intravenous bags, support structures or freestanding pumps capable of being placed on the floor or other sites within the operating theatre. By operating as a stand-alone device, the pump provides greater flexibility in terms of use and/or placement during procedures. Additionally, the pump may be disposable, if desired, thereby reducing capital costs since the valve or probe portions of the system may be reused.

Another embodiment of the present invention includes a trumpet valve in combination with a motor driven by the available suction power. Yet another embodiment includes an air motor, such as a turbine, in combination with a trumpet valve. The air motor is connected by a device such as a shaft to a pump that is used to provide pressurized fluid to the surgical site.

A preferred method of operation of the devices of the present invention is described herein. As discussed, the pump is preferably a stand-alone pump separate from the valve or probe portions of the fluid delivery system. As such, when irrigation is required, a valve piston head, connected to the operative stem of an irrigation valve, is depressed. The air motor then activates the pump, and the pumping action provides the force to drive the irrigating fluid under pressure to the surgical site. In is noted that the pump may or may not be running all the time. The selection as to whether or not the pump runs continuously depends on the relative dimensions of the pump. However, irrigation is delivered to the surgical site when the valve is depressed. The force of the fluid and amount of fluid provided are controlled by the length of depression of the valve piston head. Preferably, the valve piston head is part of a trumpet valve.

According to one mode of operation, when suction of debris is desired, the irrigation valve is released, closing the irrigation device and stopping the pump. The other valve piston head is then depressed, activating the suction function. The debris is then removed from the surgical site and displaced into an attached receptacle that is separate from the devices of the present invention and the surgical field. In a most preferred embodiment, the connections used in the present invention are connections to the irrigation fluid source and to the suction source.

Alternatively, the vacuum-driven pump may be integrated with the device by which the irrigating and suction functions are operated, such as a trumpet valve. In this embodiment, the pump and valve are included as one unit wherein depression of one of the trumpet pistons directly results in the activation of the irrigation or suction functions of the device.

The devices of the present invention may be made of any material, though preferably, the devices are made from plastic and may be easily manufactured. The material may be transparent, translucent or opaque. Most preferably, the devices of the present invention are disposable so that sterility is assured and costs are lower. The present invention contemplates embodiments that can be reused by sterilization following each use of the device. The costs of the present invention are significantly lower than that of devices currently available because there is no need for an external power source. Additionally, when the present invention is used as a stand-alone pump, the pump and the motor may be constructed to be separate so that only the pump and the trumpet valve are disposed of while the motor may be reused, lowering costs as well.

As stated previously, the most preferred embodiments of the present invention utilize devices including the pumps of the present invention wherein the pumps are stand-alone and are separate from the valve device. For example, the air motor and pumping device could be in a separate housing adjacent the valve device. See FIGS. 6 through 10 for embodiments of the present invention wherein the pump is separate from the valve or control device.

Figure 11:
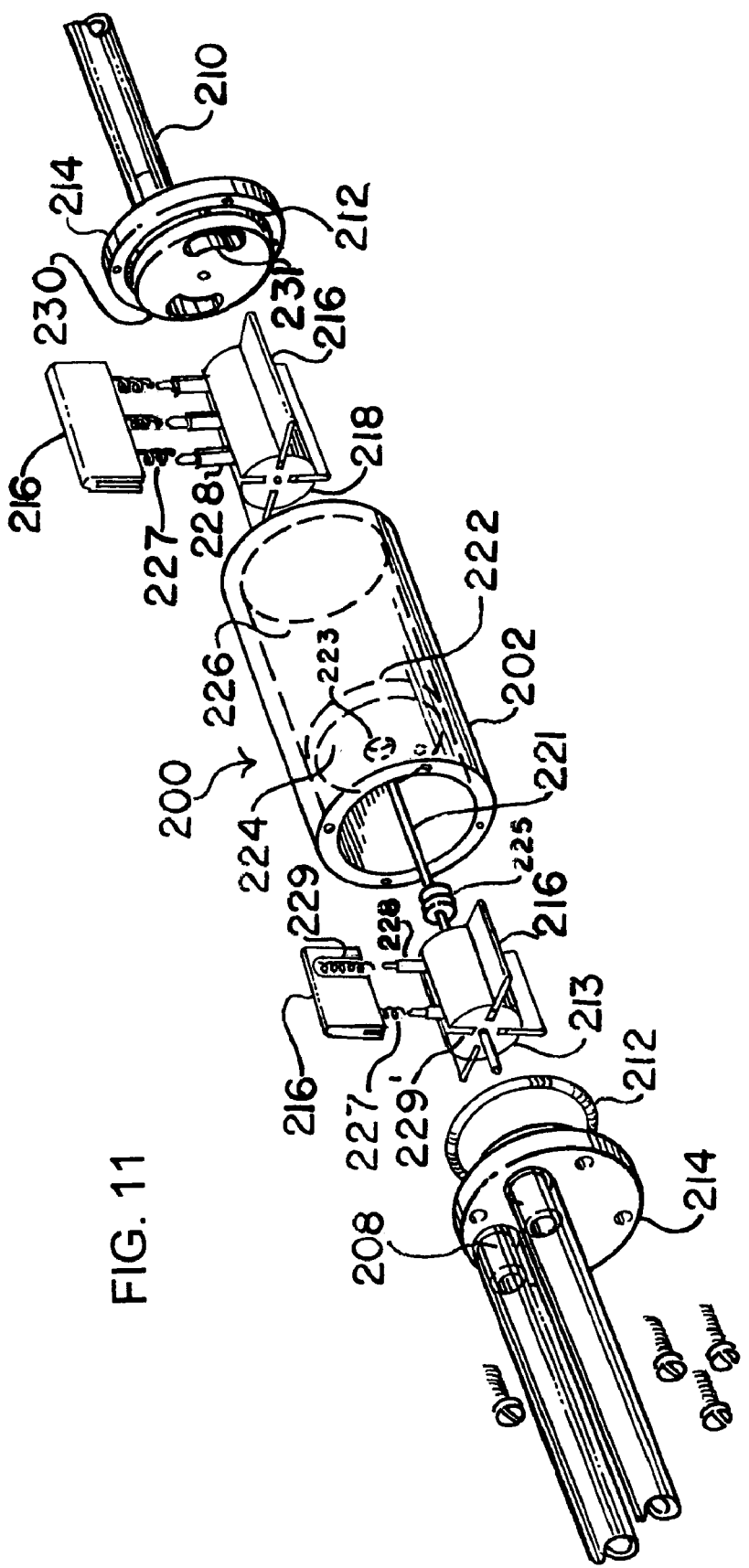
FIG. 11 is an exploded, perspective view of a stand-alone pump according to one embodiment of the present invention.

The motor driving the vacuum pump includes a rotary device having a hub and blades that adjust depending on the location of the blade in relation to the pump chamber. This is as a result of the hub being offset from the middle of the pumping chamber. Being offset permits the blades to rotate due to air drawn through into the chamber by operation of the vacuum suction action. In a preferred embodiment, the blades are offset from each other on the hub at 90° angles and the blades are not connected but ride on springs. The springs are placed in the hub such that the blades may move in and out. Accordingly, when one blade is pushed toward the hub, such as by the inner wall of the pump chamber, the corresponding blade on the other side is pushed away from the hub and into the path of the air, thereby causing the blade to be pushed, turning the rotary piston to power the device. One embodiment is shown in FIG. 11, wherein the pump includes two sets of two blades, wherein one set of blades is perpendicular to the other. However, while four blades are shown, the number of blades may vary, but are preferably even in number.

Alternatively, the present invention includes pumps having vanes and a rotor on the center line of the pumping chamber.

Alternatively, the motor driving the pumping device could be run by sources other than vacuum, such as air pressure, that is any pneumatic source. Other types of air motors that are contemplated by the present invention include, but are not limited to, roots, rotary piston, rotary screw, liquid ring and turbines. Those motors can be constructed to run off a vacuum source to drive the irrigation fluid. The present invention contemplates the use of any construction for the combined suction and irrigation device, including but not limited to structures such as a standard trumpet valve structure, a pistol grip or a wand-type housing. The structures of the present invention can be changed to meet the needs of the surgical procedures, including but not limited to, laparoscopy, open surgery, orthopedics, oral surgery, arthroscopy, endoscopy, wound cleansing, liposuction and gynecology.

The present invention also facilitates the incorporation of additional elements such as electrocautery, laser attachments, ultrasound attachments, provision of light to the surgical field, attachments for viewing the site, photography or videography of the site, computer mapping of the site, provision of pharmaceuticals, chemotherapeutics or other medicinal compositions to the site, and selective dissection or biopsy capabilities at the surgical site.

An embodiment of the present invention is shown in FIGS. 1–5. This embodiment incorporates the pump with the valve in a single system. The valve, motor and pump are combined in an easily held device that can be operated by either left-handed or right-handed clinicians. The valve is a trumpet-style valve configuration with one chamber connected to both the irrigation and suction sources. This chamber controls the pump and provides the irrigation fluid under pressure to the surgical site. The other chamber is constructed to control the suction action of the device. The trumpet valve and pump configuration TVP has a common housing for the pump and the valve.

The present invention also contemplates devices and methods of use wherein the irrigating fluid is delivered in uniform, pulsatile or other methods or combinations of such methods. Provision of irrigating fluid in such various methods may include adaptors for providing the fluid in the desired method.

Figure 2:
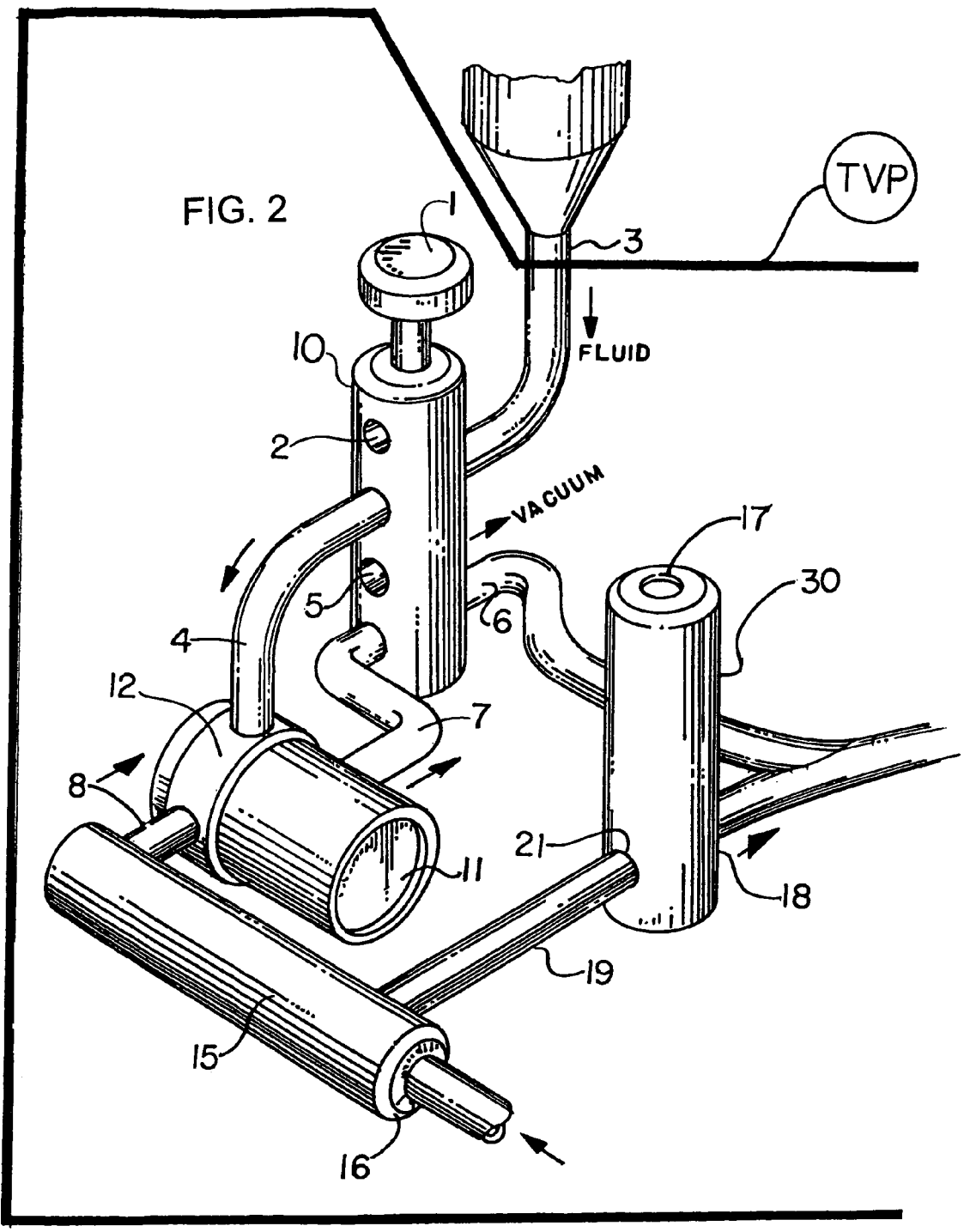
FIG. 2 is a view similar to FIG. 1 in which an irrigation valve is open.

Referring now to the figures of the drawings in detail and first, particularly, to FIG. 1 thereof, there is seen a trumpet valve and pump combination TVP having a valve stem head 1 movably displaced within a valve body 10 and connected to tubes 2 and 5 traversing the interior of valve body 10. The valve stem head 1 is depressible and operates to open a connection to the tube 2 to allow irrigation fluid to flow from the source through tube 3, through tube 2 and into tube 4. When valve stem head 1 is depressed, tube 5 is then connected to tube 6 on one side and tube 7 on the other side. This connection allows suction force to be applied from the vacuum source through tube 6, through tube 5 (through valve body 10) and into vacuum motor 11. This is illustrated in FIG. 2. When valve stem head 1 is depressed, suction force is used to operate vacuum motor 11, which in turn, powers pump 12. Irrigation fluid flowing though tube 4 into pump 12, is pressurized by pump 12 and flows out of pump 12 and into common chamber 15 through tube 8. Common chamber 15 is connected to a probe or other instrument or tubing at fitting 16.

Figure 3:
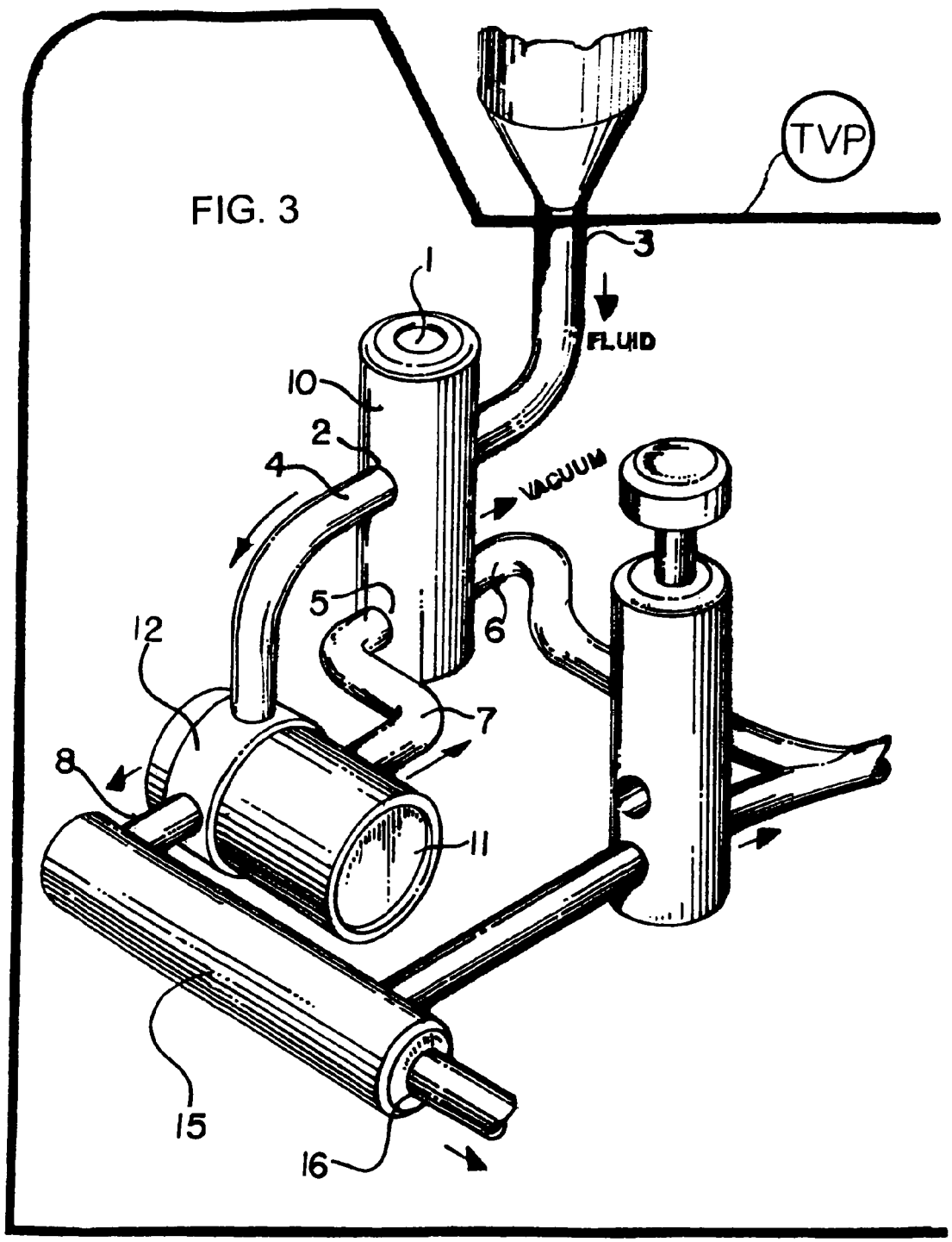
FIG. 3 is another view similar to FIG. 1 in which a suction valve is open.

In FIG. 1, valve stem head 17 is movably displaced within valve body 30 and is connected to tube 21 traversing the valve body 30. Depressing valve stem head 17 opens the connection between tube 18, which is connected to the suction source, and tube 19, which is connected to common chamber 15 by aligning the first opening of tube 21 with the opening of tube 18, and aligning the second opening of tube 21 with the opening of tube 19. Depressing valve stem head 17 creates a suction force in the probe, instrument or tubing attached to fitting 16. This is shown in FIG. 3.

Figure 4:
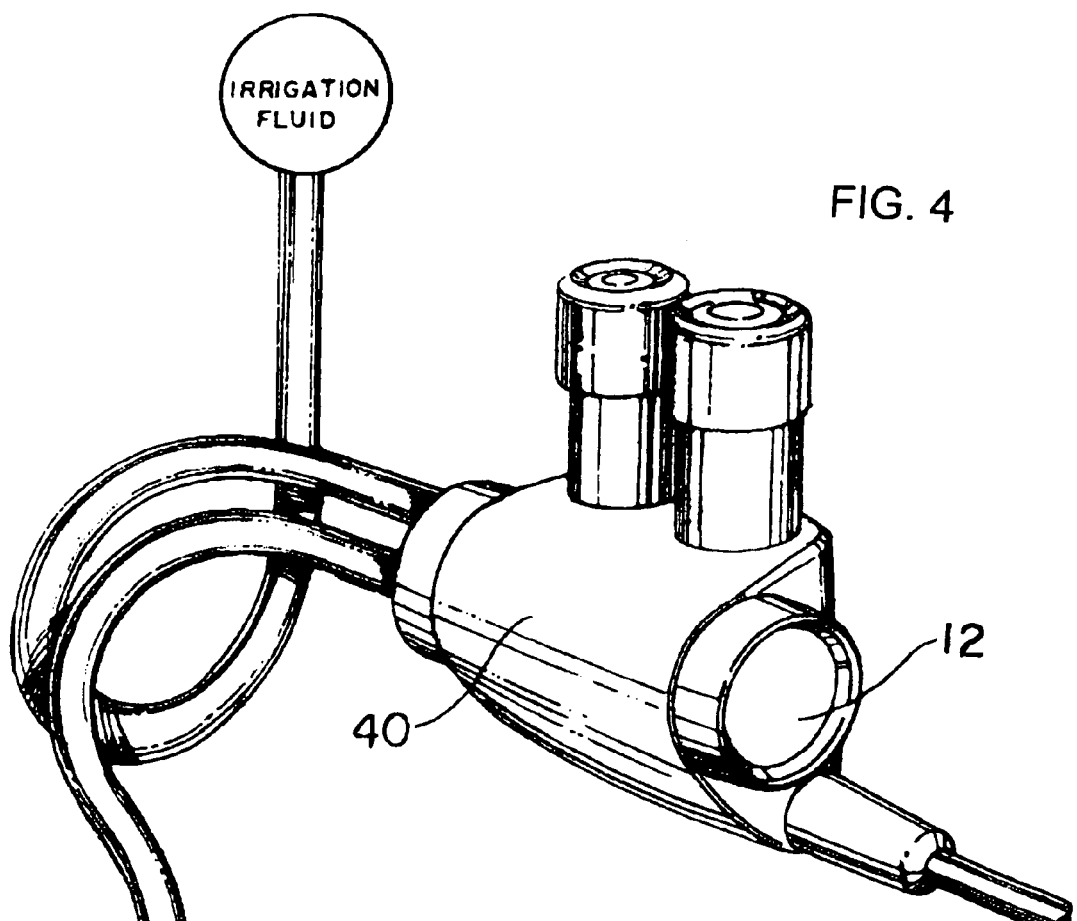
FIG. 4 is an external, perspective view of an embodiment of the trumpet valve and pump combination of the present invention.
Figure 5:
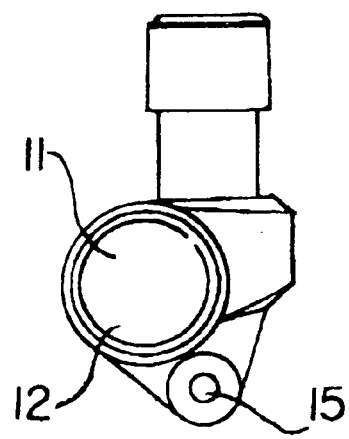
FIG. 5 is an external, side-elevational view of an embodiment of the present invention.

FIG. 4 shows an external view of a preferred embodiment of the present invention having a common housing 40, which may be transparent to permit monitoring of a pumping operation. FIG. 5 shows a fragmentary, side-elevational view of the embodiment of FIG. 4 which illustrates the placement of suction (vacuum) motor 11, pump 12 and common chamber 15.

The present invention relates to suction/irrigation devices for surgical procedures and methods of using such devices. The present invention includes devices that are easy to set-up and that have reduced complexity due to the method of powering since no additional external power source is necessary. The present invention includes lightweight, inexpensive, disposable pumps that are driven by alternative power sources.

Figure 6A:
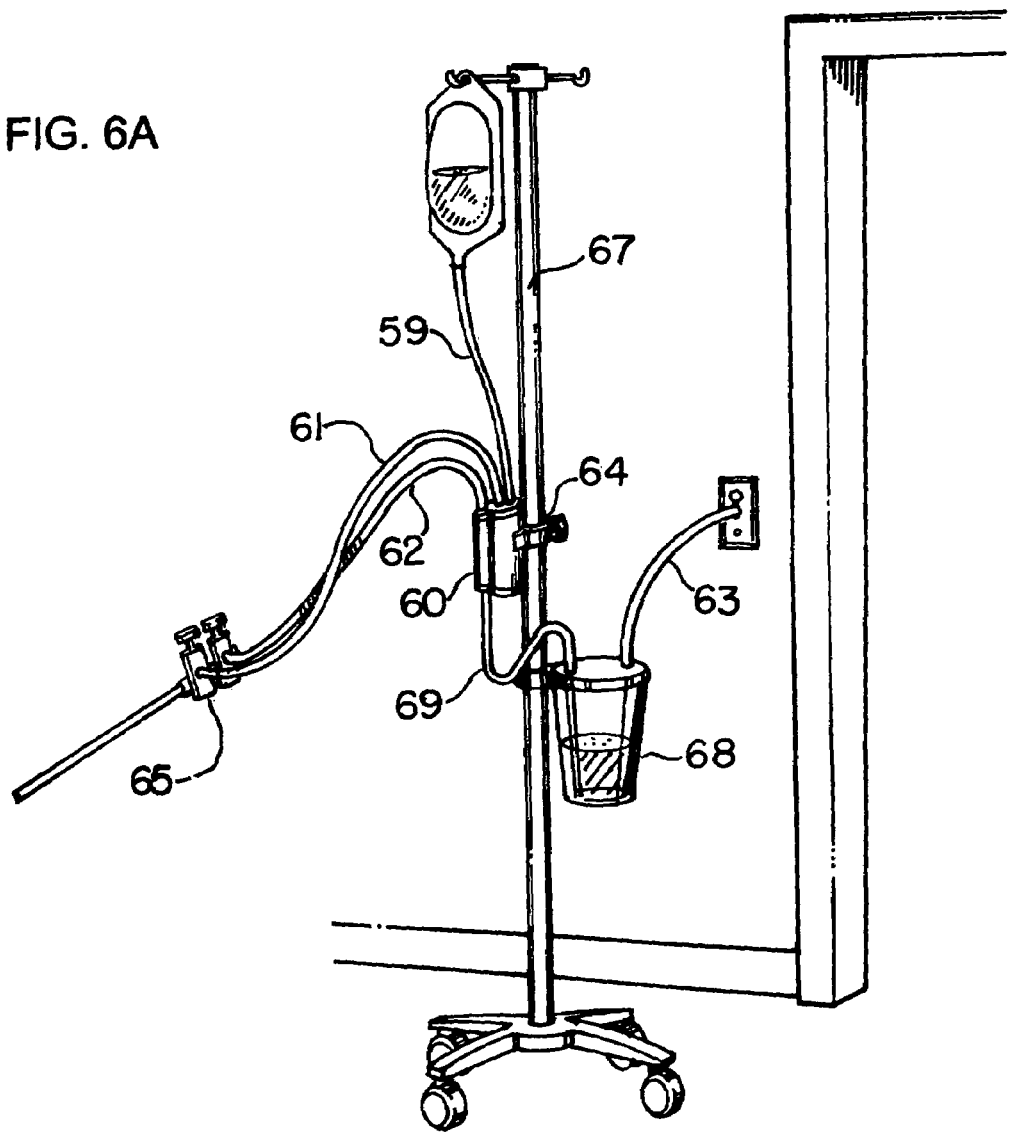
FIG. 6A is a perspective view of an embodiment of the present invention attached to a support pole such as those commonly used in operating theatres.
Figure 6B:
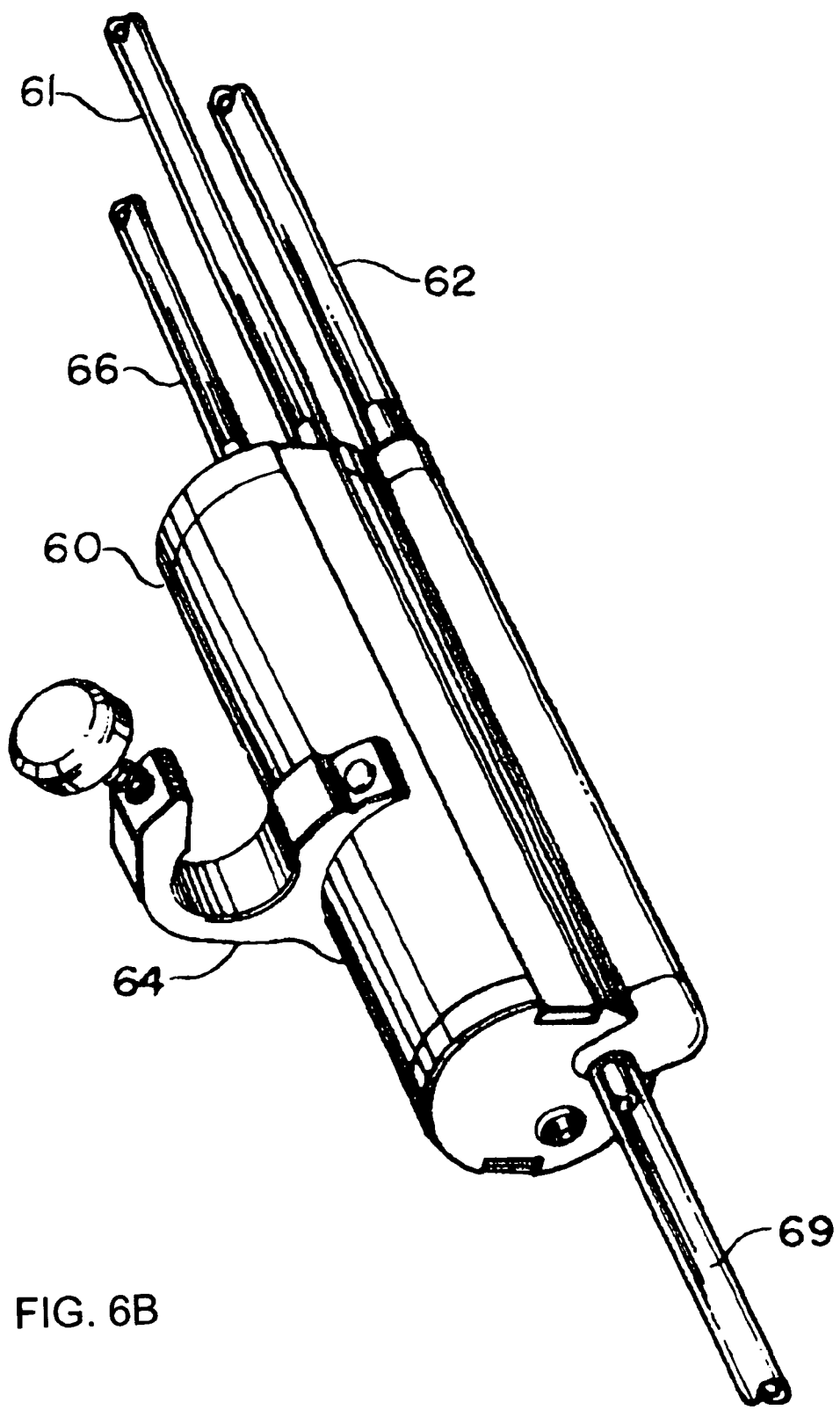
FIG. 6B is an enlarged, perspective view of the pump shown in FIG. 6A.

FIGS. 6A to 10 depict various preferred embodiments of the present invention as used in different procedures and in different manners. FIG. 6A shows a pump 60 which has an irrigation source connection 61 and a suction source connection 62 and is directly attached to a support pole 67. The support pole 67 is of the type commonly used in operating theatres, using a coupling device 64, such as a spring loaded clamp. Additionally, a suction source 63 and a container 68 may be included. As can be seen, the pump 60 is a stand-alone pump separate from the trumpet valve 65. FIG. 6B is an enlarged, perspective view of the pump 60, showing the clamp 64, the irrigation source connection 61, the suction source connection 62, an IV bag connection 66 and a suction connection 69 leading to the container 68.

FIG. 7 shows a pump 70 having an irrigation source 71 and a suction source 72 and a male 73 and female 74 bracket that permits attachment of the pump to a wall or other structure support device.

Figure 8:
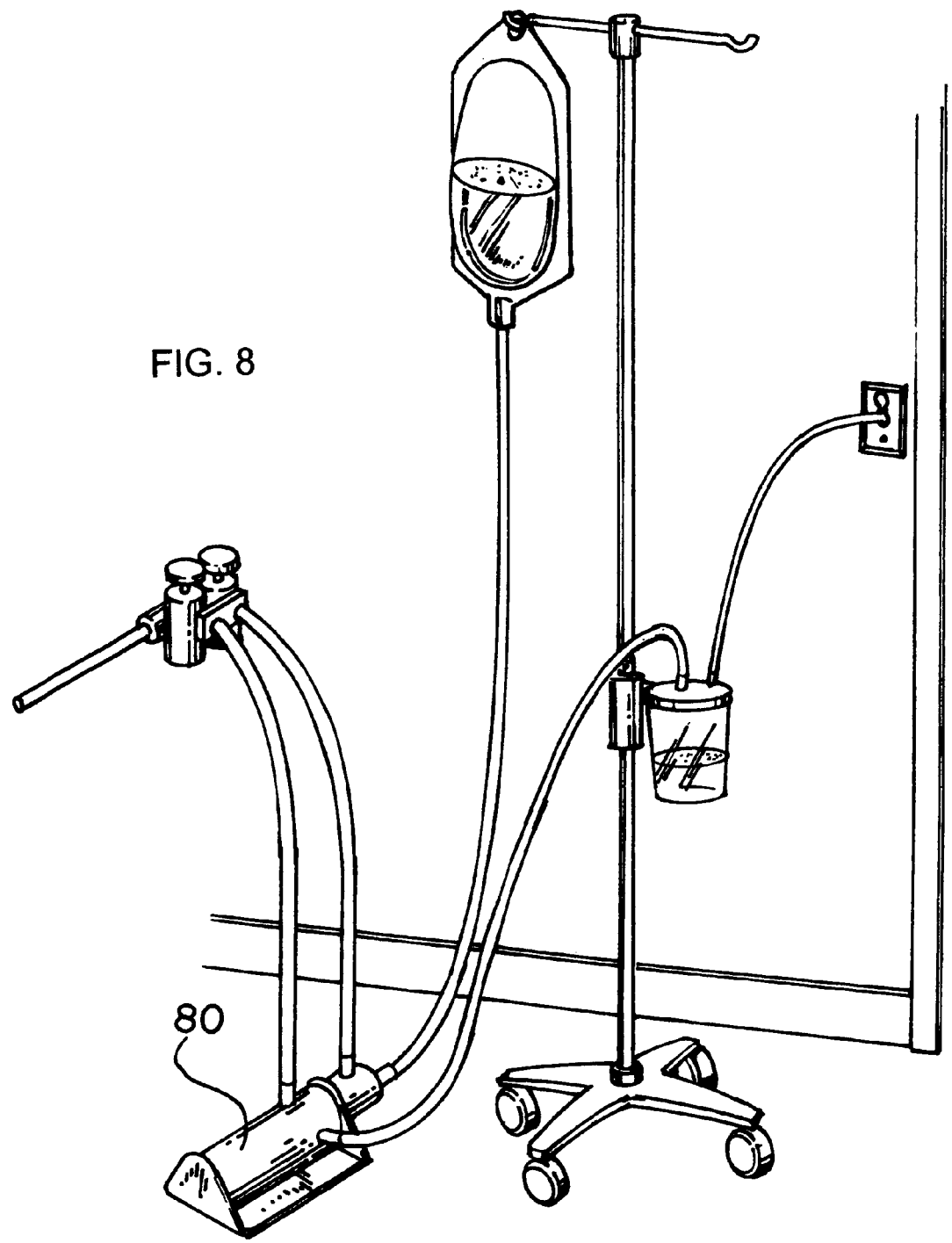
FIG. 8 is a perspective view of an embodiment of the present invention capable of being freestanding without other support structures.
Figure 9:
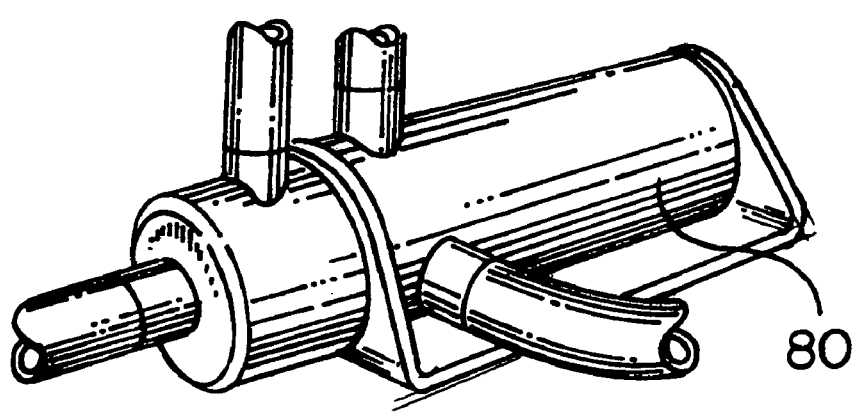
FIG. 9 is an enlarged, perspective view of the pump shown in FIG. 8.
Figure 10:
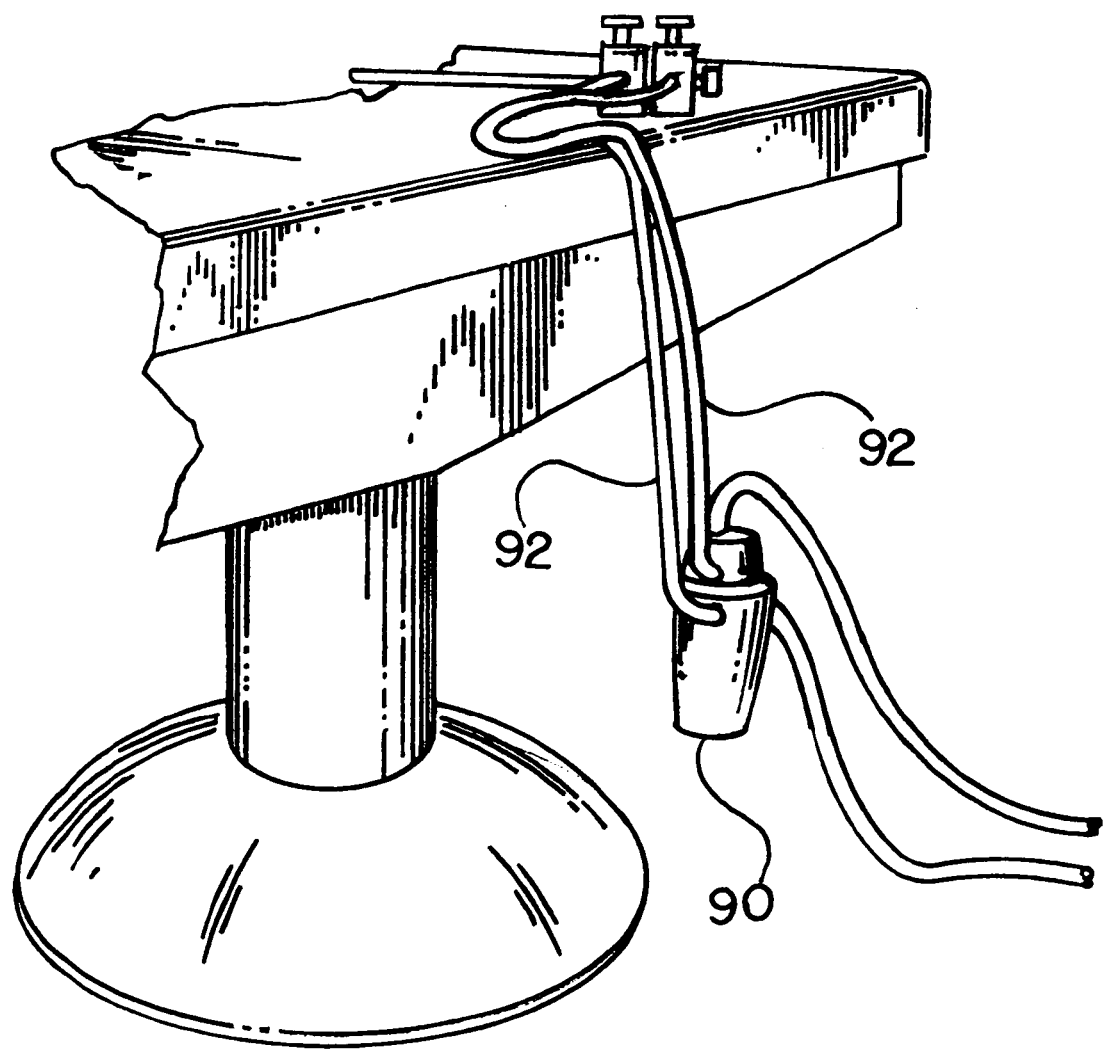
FIG. 10 is a fragmentary, perspective view of an embodiment of the present invention that is incorporated in-line with tubing.

FIG. 8 shows a freestanding pump 80 having no other support structures, FIG. 9 is an enlarged view of the pump of FIG. 8, while FIG. 10 shows an in-line pump 90 that simply hangs on tubing 92.

FIG. 11 shows an exploded view of a stand-alone pump according to the preferred embodiment of the present invention. The pump 200 includes a body or barrel 202, a liquid inlet 208, a vacuum line inlet 210 and O-rings 212 for sealing end caps 214. The pump body or barrel 202 may be transparent to permit monitoring of a pumping operation. Blades 216 and a hub 218 of a rotor, which may be used for a vacuum motor and for a liquid pump, may be of the same or different sizes. One can see that the moving vanes or blades 216 and hub 218 toward the right in the figure are to be disposed in an air motor chamber 226. Similarly, the moving vanes or blades 216 and hub 218 toward the left in the figure are to be disposed in a liquid pump chamber 224. The pump may also be of another construction, such as a centrifugal pump. The pump 200 also includes a dividing web wall 222 inside the pump body or barrel 202 that unevenly divides the air motor chamber 226 from the liquid pump chamber 224. The web wall 222 has an opening 223 formed therein which accepts a seal 225 on a drive shaft 221 supporting both hubs 218, for the motor and the pump. The opening 223 is formed off-center in the web wall 222 to allow the rotors, that is the combined hubs and blades, to rotate eccentrically in the respective chambers 224, 226.

Figure 12:
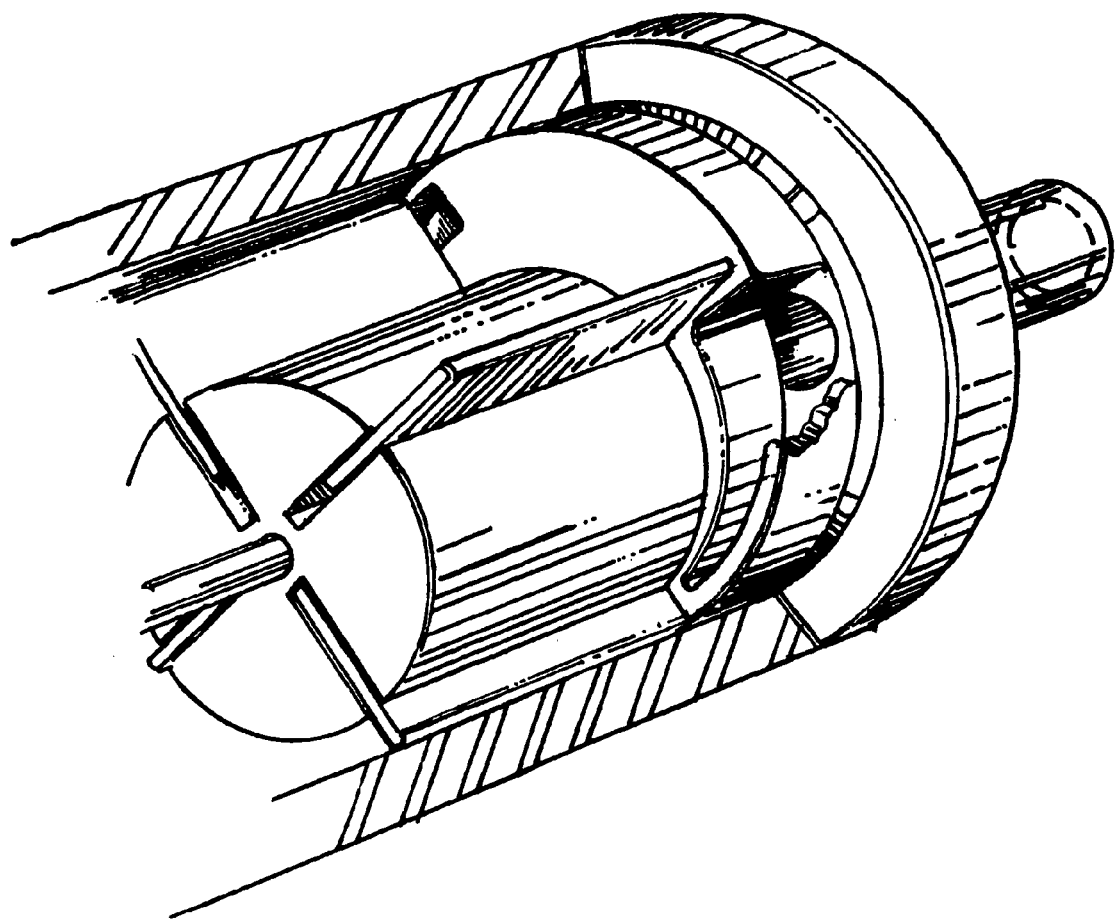
FIG. 12 is a fragmentary, partly broken-away and partly sectional, perspective view of a portion of the pump.

The blades 216 are resiliently connected to the hub 218 by springs 227 partially inserted in blind bores 229 in the blades and fitting over nipples of posts 228 inserted in blind bores 229' in the hub 218. It may also be seen that kidney-shaped pockets 230, 231 are recessed in the end caps 214. The perspective view of FIG. 12 is partly broken-away to show the blades, hub, pockets and ports to be described in greater detail below.

Figure 13A:
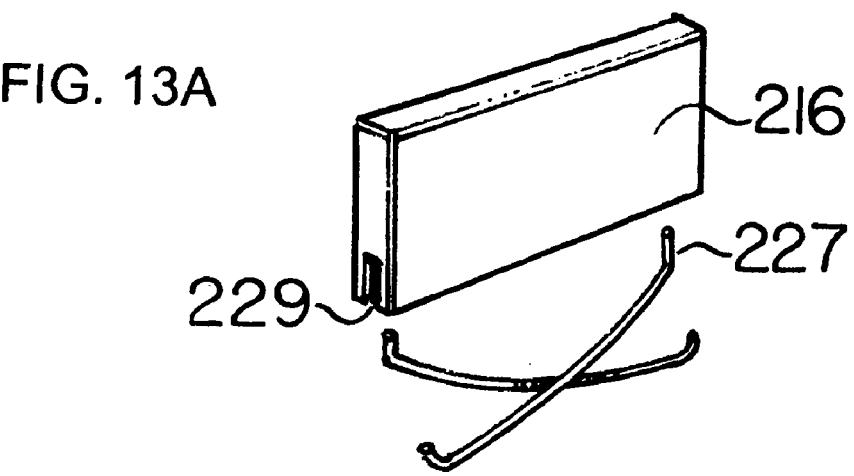
FIGS. 13A, 13B and 13C are perspective views of various valve spring structures.
Figure 13B:
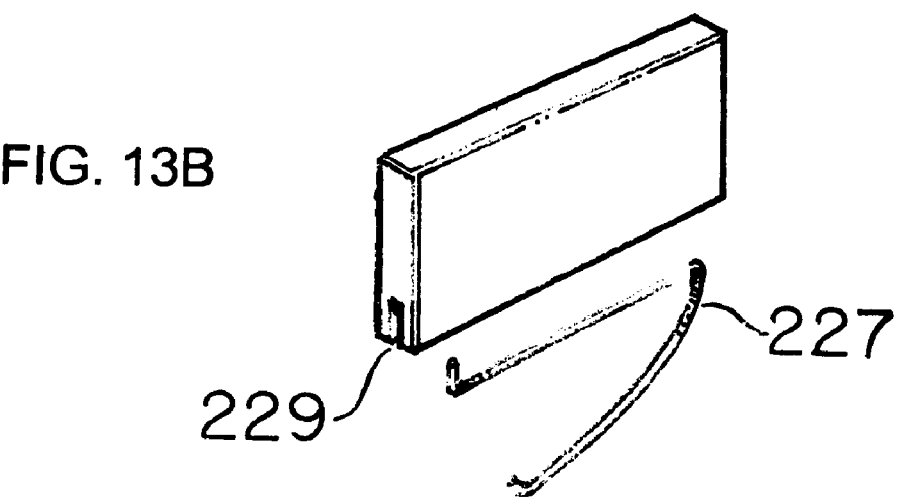
Figure 13C:
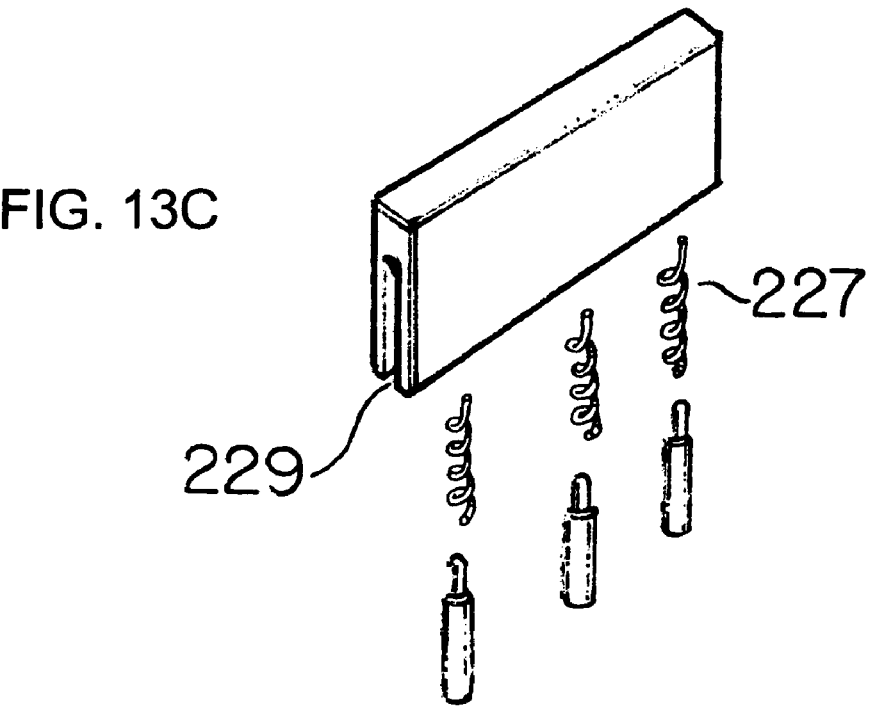

FIGS. 13A, 13B and 13C show various configurations of respective springs 227, 227a and 227b. FIG. 13A shows two leaf springs 227a in an X-shaped configuration, wherein one end of each of the springs is to be inserted into a respective blind bore 229 in a blade 216 while the other end is to be inserted into a respective blind bore 229' in the hub 218. The blind bores 229, 229' may each be in the form of one continuous slot in the blade and the hub, respectively. The leaf spring 227b of FIG. 13B has an approximately V-shape so that one end is to be inserted into a respective blind bore 229 in a blade 216 or one leg of the V-shape may be inserted into a continuous slot in the blade as described above. Similarly, the other end or leg of the V-shape may be inserted into a respective bore or slot in the hub. The illustration of FIG. 13C is an enlarged view of a portion of FIG. 11 showing the spring 227 and bores or slot.

FIG. 14A illustrates an alternative configuration of blade assemblies 316, 317 and a hub 318. It can be seen that the blade assemblies 316, 317 each include two blades and are inserted into respective slots 319, 320. The blade assemblies 316, 317 each have a respective cross-piece 314, 315 disposed at different locations along the blades. The blade assembly 317 is inserted before the blade assembly 316, so that the cross-piece 315 can be disposed further inwardly and the cross-piece 314 can be disposed further outwardly.

FIG. 14B is a cross-sectional view showing a blade 216 in a bore 229'. A spring 227 has one end on a post 228 in the bore 229' and another end in a bore 229 in the blade 216.

An end adapter 321 shown in FIG. 14D is inserted and secured into an open end of the hub 318 after the blade assemblies 316 and 317 are inserted into their respective slots, providing a shaft post.

FIG. 14C is a side-elevational view of one of the hubs 218 having three bores 229' shown in phantom. FIG. 14B is taken along a line XIVB—XIVB of FIG. 14C, in the direction of the arrows.

Figure 15A:
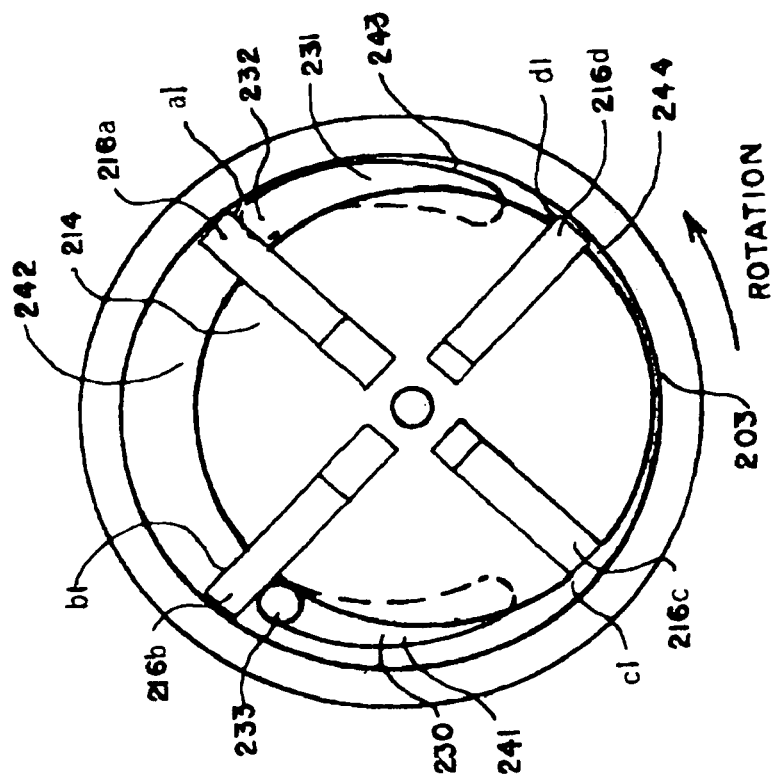
FIGS. 15A, 15B and 15C are cross-sectional views of a portion of a valve blade and barrel assembly in different phases of rotation.
Figure 15B:
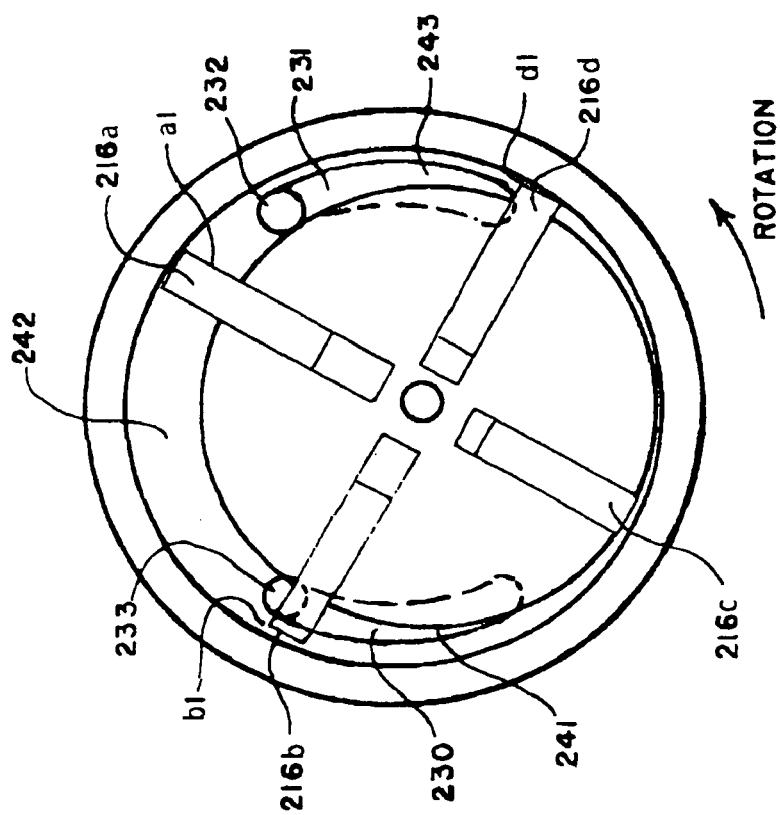
Figure 15C:
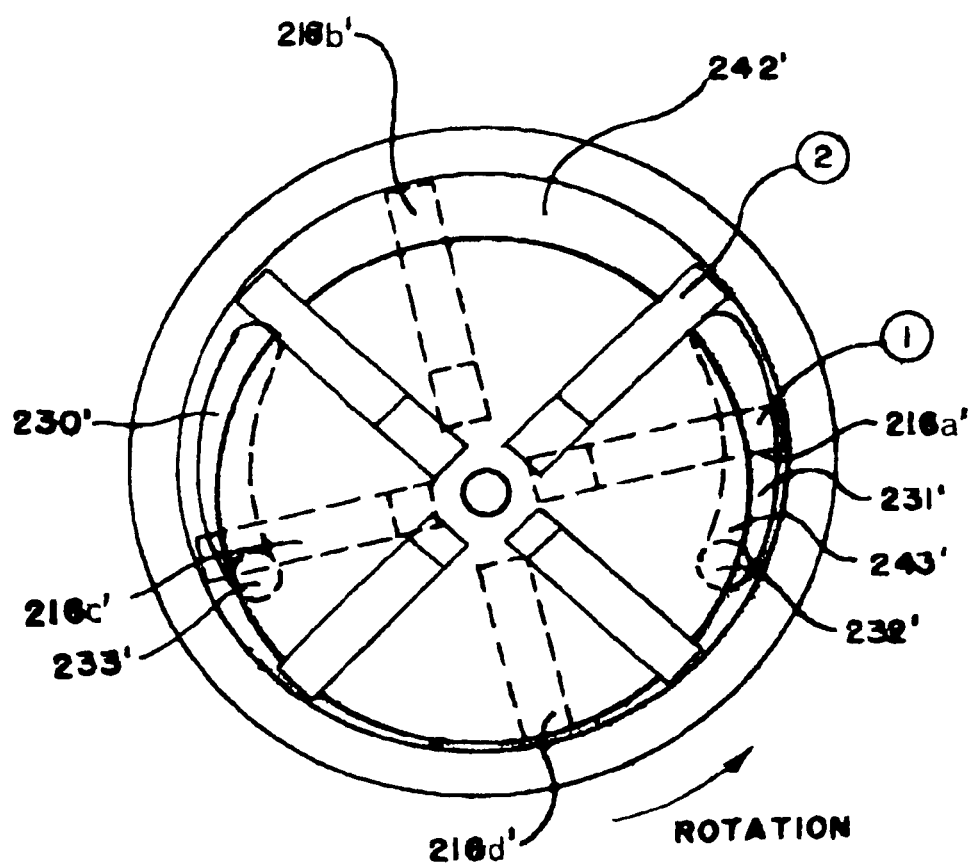

FIGS. 15A, 15B and 15C are cross-sectional views illustrating the operation of the blades 216 in the body or barrel 202 of the pump 200 of FIG. 11. The body or barrel 202 has an inner wall surface 203. The ends of the blades are biased against the inner wall surface 203 by the springs 227. The hub 218 is only diagrammatically illustrated by transverse lines within the blades for simplicity, but the seal 225 is shown. The blades have been given reference numerals 216a, 216b, 216c and 216d for use in the following explanation. The kidney-shaped pockets 230, 231 in one of the end caps 214 are shown as well. Finally, ports 232, 233 are shown leading through the end cap 214.

The following is a description of the operation of the pneumatically driven fluid pump. The device includes a pneumatic vane-type motor directly coupled to a vane-type pump used for pumping fluids.

The operation of the device as a motor will initially be described with reference to FIGS. 15A and 15B. As mentioned above, the springs 227 bias the blades 216a–216d in contact with inner wall surface 203 of the body or barrel 202. The blades 216a–216d define rotor blade cavities 241–244 therebetween within the body or barrel 202. The pockets 230, 231 connect the ports 233, 232 to the cavities 241–244. It is assumed that the blades 216a–216d in FIG. 15A are affected by a vacuum supplied to the port 233 and the port 232 is opened to the atmosphere. The vacuum fills the pocket 230 and the rotor blade cavity 241, causing a force to be exerted on a blade face b1 of the blade 216b. Since the resulting forces are directly related to the area of the blades exposed to the cavity on which the vacuum acts, the resulting force causes a turning moment or torque on the rotor in a counter clock-wise direction moving it to a position shown in FIG. 15B. In FIG. 15A, the blade 216a and the blade 216b have isolated the ports preventing air from passing from the port 232 to the port 233. In FIG. 15B, the position of the blade 216a blocks communication between the port 232 and the port 233, and the position of the blade 216b opens access to the port 233 allowing air to escape. As the rotor turns in FIG. 15B, a blade face a1 of the blade 216a has a greater area than a blade face d1 of the blade 216d, generating a larger force on the blade 216a than on the blade 216d, again turning the rotor in a counter-clockwise direction. The porting is symmetrical and applying a vacuum to the port 232 will rotate the motor in a clockwise direction.

The operation of the device as a pump will now be described. A vane motor can also be operated as a vane pump. FIG. 15C shows the pump blades in two positions, indicated as position 1 in broken lines and position 2 in solid lines. In the position 1 in FIG. 15C, the fluid applied to the port 232' fills the kidney shaped pocket 231' in the end cap and also flows into the rotor blade cavity 242' between the blades 216a' and 216b' and into the cavity 243' between the blades 216a' and 216d'.

The blades are rotated counterclockwise into the position 2 in FIG. 15C. The pockets 231' and 230' are now isolated from each other and fluid is trapped in the cavity 242'. Further rotation of the blade 216b' uncovers the upper end of the pocket 230', which contains the exit port 233'. As the rotor and the blades continue to turn, the volume in the cavity 242' decreases, forcing the fluid out of the port 233'. During rotation, the volume of the cavity between the blades 216a' and 216d' is increasing, drawing fluid from the port 232' into the pocket 231' and into the cavity 243' between the blades 216a' and 216d'.

Figure 16:
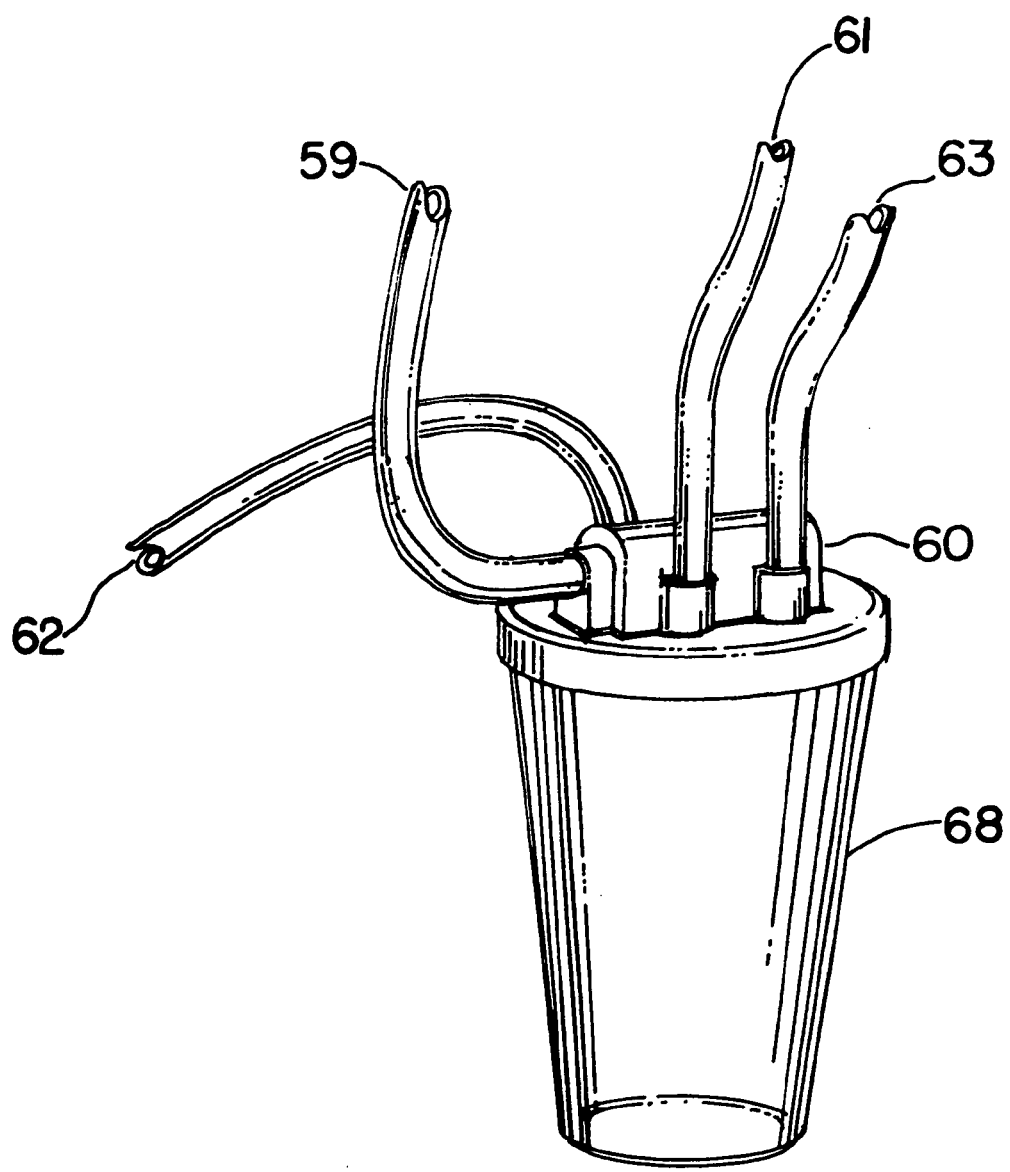
FIG. 16 is a perspective view showing the pump as an integral part of a top cover of a suction canister.

FIG. 16 shows an embodiment in which the pump 60 is an integral part of a cover of a suction canister 68. This figure shows the suction source 63, the tubing carrying the fluid to the trumpet valve from the pump 61, the line to the IV bag source of fluid 59 and the suction line to the trumpet valve 62.

It should be understood, of course, that the foregoing relates only to preferred embodiments of the present invention and that numerous modifications or alterations may be made therein without departing from the spirit and the scope of the invention as set forth in the appended claims.

What is claimed is:

1. A pump, comprising:
   a pumping chamber having an inlet;
   a rotating hub and blade assembly disposed in said pumping chamber, said rotating hub and blade assembly including blades being mutually offset on said hub at substantially 90° angles, each of said blades being fixed to said hub by a connecting device;
a connection to a fluid source; and
a connection to an air source.

2. The pump according to claim 1, wherein the fluid source is an irrigation source and the air source is a suction source.

3. The pump according to claim 1, further comprising a pump body enclosing said pumping chamber and said rotating hub and blade assembly.

4. A pump, comprising:
a pumping chamber having an inlet;
a rotating hub and blade assembly disposed in said pumping chamber;
a dividing wall defining and separating said pumping chamber from an air motor chamber;
another rotating hub and blade assembly disposed in said air motor chamber;
a connection to a fluid source; and
a connection to an air source.

5. The pump according to claim 4, wherein said pumping chamber and said air motor chamber defined by said dividing wall have different volumes.

6. The pump according to claim 4, further comprising a shaft passing through said dividing wall and having a seal sealing said shaft at an opening in said dividing wall, said shaft connected to said rotating hub and blade assembly.

7. A pump, comprising:
a pumping chamber having an inlet;
a rotating hub and blade assembly disposed in said pumping chamber, said rotating hub and blade assembly in said pumping chamber including blades being mutually offset on said hub;
an air motor chamber having an inlet;
a rotating hub and blade assembly disposed in said air motor chamber, said rotating hub and blade assembly in said air motor chamber including blades being mutually offset on said hub;
each of said chambers having a respective end cap, said end cap of said air motor chamber having ports and blind pockets formed therein for conducting air to create different pressures at surfaces of said blades in said air motor chamber for rotating said blades;
a connection to a fluid source; and
a connection to an air source.

8. The pump according to claim 7, wherein said blades are biased against an inner wall surface of said air motor chamber by springs.

9. The pump according to claim 8, further comprising posts inserted in bores formed in said hub and engaging one end of said springs, another end of said springs being inserted in said bores formed in said blades.

10. A pump, comprising:
a pumping chamber having an inlet;
a rotating hub and blade assembly disposed in said pumping chamber;
a pump body enclosing said pumping chamber and said rotating hub and blade assembly, said pump body being transparent for visually monitoring a pumping operation;
a connection to a fluid source; and
a connection to an air source.

11. A method for providing fluid, which comprises:
a) providing a pump having a rotating hub and blade assembly and being connected to a source for fluid and a source for air, the rotating hub and blade assembly including blades being offset from one another on the hub at substantially 90° angles, each of the blades being fixed to the hub by a connecting device ensuring constant spacing between the blades;
b) driving the pump with a vacuum; and
c) pumping the fluid to a site.

12. The method according to claim 11, wherein the fluid source is an irrigation source, the air source is a suction source and the site is a surgical site.

13. The method according to claim 11, wherein the pump includes a pump body enclosing the rotating hub and blade assembly.

14. The method according to claim 11, further comprising carrying out the method in a procedure selected from the group consisting of laparoscopy, open surgery, orthopedics, oral surgery, arthroscopy, endoscopy, wound cleansing, liposuction and gynecology.

15. A method for providing fluid, which comprises:
a) providing a pump having a rotating hub and blade assembly and being connected to a source for fluid and a source for air;
b) biasing blades of the rotating hub and blade assembly against an inner wall surface of an air motor chamber containing the rotating hub and blade assembly;
c) driving the pump with a vacuum; and
d) pumping the fluid to a site.

16. The method according to claim 15, which further comprises admitting air through ports and blind pockets formed in an end cap of the air motor chamber to create different pressures at surfaces of the blades for rotating the blades of the rotating hub and blade assembly.

17. The method according to claim 15, wherein the fluid source is an irrigation source, the air source is a suction source and the site is a surgical site.

18. The method according to claim 15, wherein the pump includes a pump body enclosing the rotating hub and blade assembly.

19. The method according to claim 15, further comprising carrying out the method in a procedure selected from the group consisting of laparoscopy, open surgery, orthopedics, oral surgery, arthroscopy, endoscopy, wound cleansing, liposuction and gynecology.

20. A method for providing fluid, which comprises:
a) providing a pump connected to a source for fluid and a source for air and having a pumping chamber with a rotating hub and blade assembly and an air motor chamber with another rotating hub and blade assembly;
b) driving the other rotating hub and blade assembly of the air motor chamber with a vacuum; and
c) pumping the fluid from the pumping chamber to a site.

21. The method according to claim 20, wherein the fluid source is an irrigation source, the air source is a suction source and the site is a surgical site.

22. The method according to claim 20, further comprising carrying out the method in a procedure selected from the group consisting of laparoscopy, open surgery, orthopedics, oral surgery, arthroscopy, endoscopy, wound cleansing, liposuction and gynecology.

* * * * *